(12) United States Patent
Weiss

(10) Patent No.: US 9,841,275 B2
(45) Date of Patent: Dec. 12, 2017

(54) OPTICAL MONITORING DEVICE FOR MONITORING CURVATURE OF A FLEXIBLE MEDICAL INSTRUMENT

(75) Inventor: Steffen Weiss, Hamburg (DE)

(73) Assignee: Koninklike Philips N.V., Eindhoven (NL)

( * ) Notice: Subject to any disclaimer, the term of this patent is extended or adjusted under 35 U.S.C. 154(b) by 206 days.

(21) Appl. No.: 14/342,799

(22) PCT Filed: Aug. 28, 2012

(86) PCT No.: PCT/IB2012/054397
§ 371 (c)(1),
(2), (4) Date: Mar. 5, 2014

(87) PCT Pub. No.: WO2013/035010
PCT Pub. Date: Mar. 14, 2013

(65) Prior Publication Data
US 2014/0211213 A1   Jul. 31, 2014

Related U.S. Application Data

(60) Provisional application No. 61/532,583, filed on Sep. 9, 2011.

(51) Int. Cl.
*G01B 11/16*    (2006.01)
*A61B 1/005*    (2006.01)
(Continued)

(52) U.S. Cl.
CPC .............. *G01B 11/16* (2013.01); *A61B 1/005* (2013.01); *A61M 25/09* (2013.01);
(Continued)

(58) Field of Classification Search
CPC ..... G01B 11/24; G01B 11/25; G01B 11/2513; G01B 11/16; A61B 1/005; G01M 5/0033; G01M 11/083; A61M 25/09
(Continued)

(56) References Cited

U.S. PATENT DOCUMENTS 4,761,073 A * 8/1988 Meltz ................... G01B 11/16
250/227.18
5,182,779 A   1/1993 D'Agostino et al.
(Continued)

FOREIGN PATENT DOCUMENTS

CN          101099657 A     1/2008
CN            1916583 B    11/2010
(Continued)

OTHER PUBLICATIONS

S. Krueger et al., "An MR Guidewire Based on Micropultruded Fiber-Reinforced Material", Magnetic Resonance in medicine 60:1190-1196 (2008).
(Continued)

*Primary Examiner* — Tarifur Chowdhury
*Assistant Examiner* — Mohamed K Amara

(57) ABSTRACT

An optical monitoring device for monitoring curvature along a flexible medical instrument including optical fibers, a light source to inject light into the optical fibers, a light receiver configured to measure an optical characteristic of reflected light from the optical fibers, a processor to analyze the measured optical characteristic to determine a curvature of the optical fibers, compare the curvature with a threshold curvature, determine a location along the optical fibers of the determined curvature, store previous curvatures and their associated location along the fibers in a storage, analyze the stored curvatures by counting or summing curvatures determined at a given location over time to predict breakdown of the flexible medical instrument, and produce an indication when the stored curvatures determined at the given location over time predict breakdown of the flexible medical instrument at the given location.

4 Claims, 2 Drawing Sheets

(51) Int. Cl.
*G01M 5/00* (2006.01)
*G01M 11/08* (2006.01)
*A61M 25/09* (2006.01)

(52) U.S. Cl.
CPC ........ *G01M 5/0033* (2013.01); *G01M 5/0091* (2013.01); *G01M 11/083* (2013.01)

(58) Field of Classification Search
USPC .................................................. 356/600–601
See application file for complete search history.

(56) References Cited

U.S. PATENT DOCUMENTS

| | | | | |
|---|---|---|---|---|
| 5,633,494 | A * | 5/1997 | Danisch | G02B 6/02057 250/227.14 |
| 5,684,297 | A * | 11/1997 | Tardy | G01D 5/35383 250/227.14 |
| 6,458,088 | B1 | 10/2002 | Hurtak et al. | |
| 7,212,694 | B2 | 5/2007 | Shin et al | |
| 7,315,666 | B2 * | 1/2008 | Van Der Spek | E21B 47/01 385/12 |
| 8,337,397 | B2 * | 12/2012 | Prisco | A61B 1/00009 600/103 |
| 8,698,886 | B2 * | 4/2014 | Hirakawa | A61B 1/005 348/74 |
| 8,784,303 | B2 * | 7/2014 | Laby | A61B 1/0052 600/117 |
| 9,057,600 | B2 * | 6/2015 | Walker | G01B 11/14 |
| 9,062,965 | B2 * | 6/2015 | Yoshida | G01B 11/165 |
| 9,069,148 | B2 * | 6/2015 | Herbst | G02B 6/4416 |
| 9,097,562 | B2 * | 8/2015 | Freitag | G01D 5/353 |
| 9,146,095 | B2 * | 9/2015 | Tsuda | G01B 11/18 |
| 9,267,330 | B2 * | 2/2016 | Rinzler | E21B 7/14 |
| 2002/0088931 | A1 * | 7/2002 | Danisch | G01B 11/18 250/227.14 |
| 2002/0183592 | A1 * | 12/2002 | Suzuki | A61B 1/00071 600/145 |
| 2003/0025912 | A1 * | 2/2003 | Hui | G01J 9/02 356/477 |
| 2003/0169956 | A1 * | 9/2003 | Lange | G01B 11/16 385/12 |
| 2004/0197050 | A1 * | 10/2004 | Lovseth | G01B 11/16 385/37 |
| 2004/0252939 | A1 * | 12/2004 | Gaylord | G02B 6/02085 385/28 |
| 2006/0013523 | A1 * | 1/2006 | Childers | A61B 1/00165 385/12 |
| 2007/0116415 | A1 * | 5/2007 | Kobayashi | A61B 5/06 385/116 |
| 2007/0156019 | A1 * | 7/2007 | Larkin | A61B 19/2203 600/104 |
| 2008/0009749 | A1 | 1/2008 | Delianides et al. | |
| 2008/0144698 | A1 * | 6/2008 | Cloutier | G01D 5/268 374/161 |
| 2008/0204706 | A1 | 8/2008 | Magne et al. | |
| 2008/0212082 | A1 * | 9/2008 | Froggatt | G01M 11/083 356/73.1 |
| 2011/0098533 | A1 * | 4/2011 | Onoda | A61B 1/0051 600/117 |
| 2011/0139447 | A1 * | 6/2011 | Ramos | E21B 47/09 166/254.2 |
| 2013/0076861 | A1 * | 3/2013 | Sternklar | G01J 1/42 348/46 |
| 2013/0083310 | A1 * | 4/2013 | Ramamurthy | A61B 5/06 356/32 |
| 2013/0167628 | A1 * | 7/2013 | Hull | G01V 1/001 73/152.58 |
| 2014/0092375 | A1 * | 4/2014 | Raghavan | G01L 1/246 356/32 |
| 2014/0211213 | A1 | 7/2014 | Weiss | |
| 2014/0218716 | A1 * | 8/2014 | Brown | G01K 11/32 356/32 |

FOREIGN PATENT DOCUMENTS

| | | |
|---|---|---|
| JP | 2000005320 A | 1/2000 |
| JP | 2003065733 A | 3/2003 |
| JP | 201050526 A | 9/2011 |
| WO | WO03008926 | 1/2003 |
| WO | WO2007000148 | 1/2007 |
| WO | WO2011003013 | 1/2011 |
| WO | WO2011059888 | 5/2011 |

OTHER PUBLICATIONS

R. Mekle et al., A Polymer-Based MR-Compatible Guidewire: A Study to Explore New Prospects for Interventional Peripheral Magnetic Resonance Angiography (ipMRA), Journal of Magnetic Resonance Imaging 23:145-155 (2006).

* cited by examiner

OPTICAL MONITORING DEVICE FOR MONITORING CURVATURE OF A FLEXIBLE MEDICAL INSTRUMENT

CROSS-REFERENCE TO PRIOR APPLICATIONS

This application is the U.S. National Phase application under 35 U.S.C. §371 of International Application Ser. No. PCT/IB2012/054397, filed on Aug. 28, 2012, which claims the benefit of United States Application Ser. No. 61/532,583, filed on Sep. 9, 2011. These applications are hereby incorporated by reference herein.

FIELD OF THE INVENTION

The invention relates to flexible medical instruments and in particular to a method and an optical apparatus for reducing the risk of kinking of such medical instrument.

BACKGROUND OF THE INVENTION

Metallic guidewires used for vascular interventions are configured to be highly bendable to enable transportation of the guidewire through vascular organs such as blood vessels. In spite of their bendable capabilities it is known that guidewires may kink, break or fracture and thereby increase the risk of vascular damage by sharp parts or loss of guidewire parts inside the patient.

Accordingly, there is a need to reduce or eliminate the risk of breakdown of guidewires.

JP 2000005320 discloses a guidewire configured in a way that the risk of permanent deformation or breakage even against bending by a small radius is reduced. The guidewire consists of a fiber-re-inforced plastic (FRP) core wire obtained by converging many fibers in an axial direction and integrating them with a synthetic resin and a synthetic resin layer coating the outer periphery of the wire. In this case, a cavity is made to exist inside the wire; thereby the optical fibers in the wire flexibly follow curving by the existence of the cavity. Thus, there is no worry about permanent deformation even against curving of a small radius and there is no worry about complete breakage even after being kinked.

Whereas JP 2000005320 discloses a guidewire configured to reduce the risk of permanent deformation or breakage due to bending, the inventor of the present invention has appreciated that other improvements for avoiding damage of guidewires would be of benefit, and has in consequence devised the present invention.

SUMMARY OF THE INVENTION

It would be advantageous to achieve improvements for avoiding breakdown failures of medical flexible instruments such as guidewires. In general, the invention preferably seeks to address such improvements by generating a warning before a breakdown occurs. Thus, it is an object of the present invention to provide a method that solves the above mentioned problems relating to guidewires, or other problems, of the prior art.

To better address one or more of these concerns, in a first aspect of the invention an optical monitoring device for monitoring curvature along a flexible medical instrument is presented that comprises, an optical fiber detector comprising one or more optical fibers, a light source for injecting light into the optical fibers, a light receiver for measuring an optical characteristic of reflected light from the optical fibers, where the optical fibers are configured so that the optical characteristic of the reflected light is affected by bending of the fibers, a processor for analyzing the measured optical characteristic for determining a curvature of the optical fiber detector, and for comparing the curvature with a threshold curvature.

The one or more fibers, such as two or more fibers, may be embedded into an elongate cladding or cover so that the fibers extend along each other without crossing, and so that they extend substantially parallel to each other.

The light source and/or the light receiver may be permanently or detachably connected to the optical fiber detector.

By comparing the determined curvature with a threshold and possibly generating some notification to the user of the flexible medical instrument in case the curvature becomes less than the threshold it may be possible to avoid further bending of the instrument and, thereby avoid possible kinking or breaking of the instrument.

In an embodiment the processor is further configured to determine a location along the optical fiber detector of the determined curvature. Advantageously, the determination of a location enables informing the user of the medical instrument where a curvature of the instrument have become smaller than the threshold and, thereby, enabling the user to decide what actions should be taken to avoid possible vascular damages.

In an embodiment the processor is further configured for storing previous curvatures and their associated location along the fiber detector. By storing measured curvatures and locations in a storage such as an electronic data storage, the history of stored values may advantageously be used for determining the risk for future breakage of the medical instrument due to material fatigue.

In an embodiment the processor is further configured to analyze the stored curvatures to predict breakdown of the flexible medical instrument. Analyzing the curvatures may comprise integrating or summing curvatures for predicting a total load of the medical instrument at different locations along the length of the instrument.

In an embodiment the breakdown is predicted by counting or summing curvatures determined at a given location over time for predicting breakdown of the flexible medical instrument.

In an embodiment the device further comprises an alarm configured to generate an alarm if a breakdown is predicted or if a determined curvature exceeds a maximal allowable curvature.

Advantageously, an alarm may be importing for notifying the user of the medical instrument that a break, kink or fracture of the medical instrument may occur if use of the instrument or bending of the instrument is continued.

A second aspect of the invention relates to a flexible medical instrument comprising the optical monitoring device according to the first aspect, where the optical fiber detector extends along the flexible medical instrument and within an outer surface of the flexible medical instrument.

The optical fiber detector may be engaged with the flexible medical instrument in various ways; the optical fiber detector or its fibers may be integrated with a braid or fiber mesh of the instrument, the detector may be contained in a lumen of the instrument which extends longitudinally e.g. along the center of the instrument, or the detector may be engaged in other ways e.g. by fixating the detector on an outer surface of the instrument. The detector may be permanently fixated to the medical instrument or the detector may be detachably connected to the instrument.

A third aspect of the invention relates to a method for monitoring curvature along a flexible medical instrument, the method comprises,
- arranging an optical fiber detector comprising one or more optical fibers (201) along the flexible medical instrument,
- injecting light into the one or more optical fibers using a light source,
- measuring an optical characteristic of reflected light from the optical fibers using a light receiver, where the optical fibers are configured so that the optical characteristic of the reflected light is affected by bending of the fibers,
- analyzing the measured optical characteristic for determining a curvature of the optical fiber detector, and
- comparing the determined curvature with a threshold curvature.

In general the various aspects of the invention may be combined and coupled in any way possible within the scope of the invention. These and other aspects, features and/or advantages of the invention will be apparent from and elucidated with reference to the embodiments described hereinafter.

In summary the invention relates to a method for predicting kinking, breaking or fracturing of flexible medical instruments such as guidewires. Fiber optic methods for determining curvature are known. However, according to this invention such optic methods can be utilized for determining bending of flexible medical instruments, for example by determining when the curvature of the flexible medical instruments becomes smaller than a given curvature threshold. The flexible medical instruments may kink, break or fracture due to material fatigue. To predict failure of the instrument due to fatigue, the bending actions on the instrument may be monitored during the entire lifetime or during several uses of the instrument for determining a warning of a possible risk of instrument failure.

BRIEF DESCRIPTION OF THE DRAWINGS

Embodiments of the invention will be described, by way of example only, with reference to the drawings, in which.

DESCRIPTION OF EMBODIMENTS

Figure 1A:
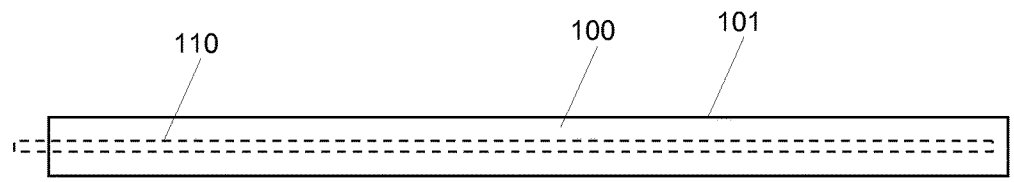
FIG. 1A-B shows a guidewire 101 with a fiber optical detector 110 for measuring values of curvature.

FIG. 1A shows a guidewire 100 used e.g. for vascular interventions in a patient's body. For example, a guidewire may be used for advancing a catheter in a vessel of a patient. The guidewire may be made of metal or non-metallic material to enable use of the guidewire in an MR scanner imaging process.

During advancing the guidewire 100 through a vessel the guidewire is exposed to bending at different locations along the length of the guidewire. A single location may be exposed to bending several times during the process. Even though the guidewire is configured to be highly flexible, is made of material which is highly resistant to repeated bending of small bending radii and has passed a fracture test (e.g. the ISO 11070 test), the guidewire may kink, break or parts of the guidewire may fracture. Particularly, fiber-reinforced guidewires for use in MR scanning process may break if the curvature radius becomes too small. The guidewire 100 may be used only once or the guidewire 100 may be used several times by cleaning the guidewire after each use.

Figure 1B:
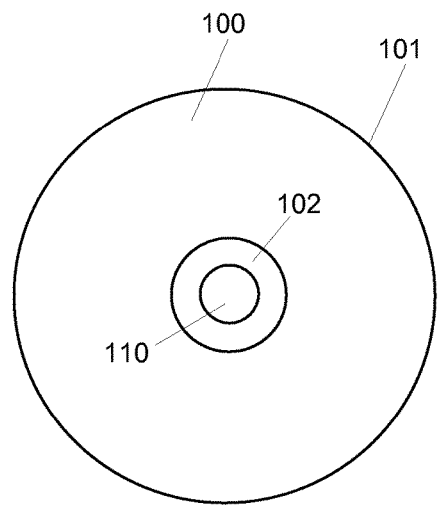

FIG. 1A shows an optical fiber detector 110 which is arranged so that it extends along the guidewire 100. The optical fiber detector 110 may be arranged so that it is contained within an outer surface 101 of the guidewire. For example, the optical fiber detector 110 may be contained in a lumen 102 of the guidewire as shown in FIG. 1B. Alternatively, the fiber detector 110 could be attached to the outer surface 101 of the guidewire 100, although this is a less preferred solution compared to the embedding of the optical fiber detector 110 in the guidewire 100.

The guidewire 100 may be manufactured with a lumen 102 dimensioned so that the optical fiber detector can be inserted and possibly removed after use. Alternatively, the guidewire 100 may be manufactured so that the fiber detector 110 is connected to or embedded in the guidewire 100 during manufacturing. Accordingly, the optical fiber detector may be fixedly or loosely connected with the guidewire 100. Thus, it is understood that the optical fiber detector may be sold as a detector for later attachment or insertion in a guidewire 100, or the fiber detector may form part of a guidewire 100 and, therefore, sold as a guidewire 100 with a fiber detector 110.

The optical fiber detector is configured so that the light which propagates in the fiber is affected by bending of the optical detector. Accordingly, by inputting light into the fiber and measuring relevant optical characteristics of light reflected from the fiber enables determination of bending and curvature values of the fiber.

Figure 2:
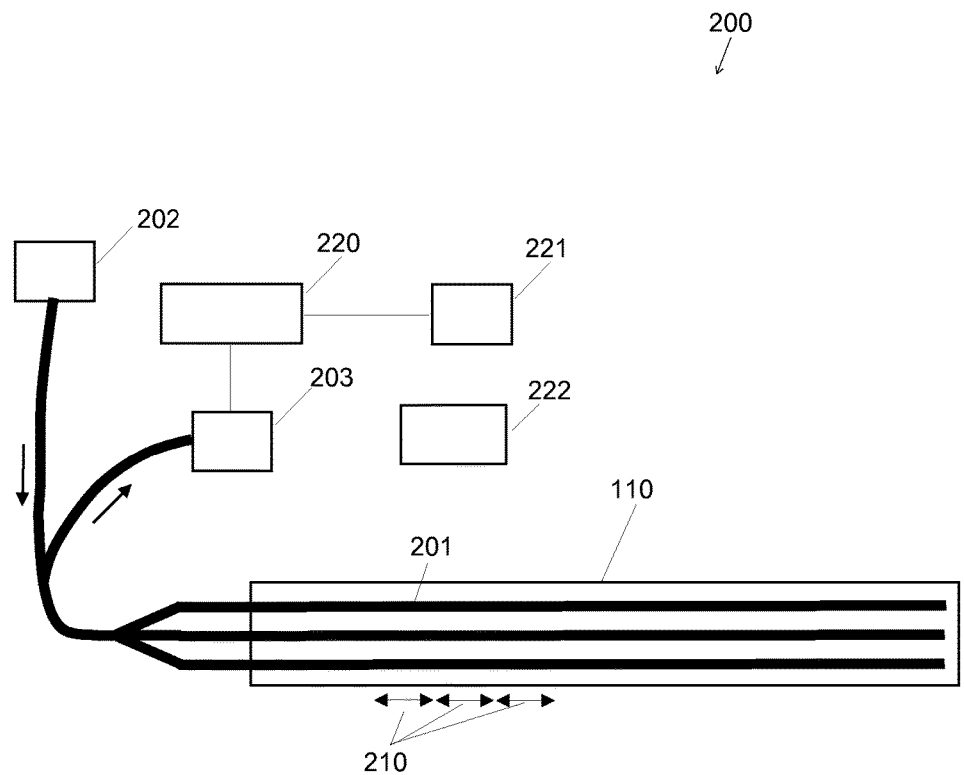
FIG. 2 shows an optical monitoring device for monitoring curvature along a flexible medical instrument.

FIG. 2 shows an example of an optical monitoring device 200 for monitoring curvature along a guidewire 100. The optical monitoring device comprises the optical fiber detector 110 which in this example has three optical fibers 201. Each fiber 201 receives light from a light source 202, which may have individual light emitters for each fiber 201 or a common light emitter which provides light for all fibers 201 as shown in FIG. 2. The light which is reflected from the fibers 201 is measured with a light receiver 203. The light receiver may have individual light detectors for each fiber 201 or a common light detector for all fibers as shown in FIG. 2. The light emitter 202 and detector 203 depicted here as two separate entities may alternatively be realized in a combined or integrated form, e.g. as an interferometer connected to the fibers 201

The fiber 201 may be a specially manufactured fiber or a standard fiber wherein fluctuations in the index profile along the fiber causes Rayleigh scattering which can be measured by the light receiver 203. For a given fiber 201, the amplitude of Rayleigh scattered light, as a function of distance, is a random but static property of that fiber and can be modeled as a long, weak fiber Bragg grating with a random period. Changes in the local period of the Rayleigh scatter caused by bending (which causes strain) in turn cause changes in the locally reflected spectrum. This spectral shift can then be calibrated to form a distributed strain sensor. The Rayleigh scattered light is interrogated similarly to Bragg gratings in that the complex reflection coefficient of a fiber as a function of wavelength is first obtained. The Rayleigh scatter as a function of wavelength is obtained via the Fourier transform. The detector 203 may comprise a storage for storing the Rayleigh scatter signature or profile of the fiber at which has been measured when the fiber is in a given state, i.e. the fiber may be straight. The scatter profile is then measured when the fiber is in a perturbed state, i.e. a bend state. The scatter profiles from the two data sets are then compared along the entire fiber length in increments of Δx. Each incremental fiber core segment represents a discrete sensing element, and can be considered a strain sensor. When a segment of fiber experiences a change in strain, the reflected spectrum from that segment shifts proportionally. To determine the amount of spectral shift, a complex cross-correlation is performed between reference data and measurement data for each fiber segment. Any change in strain manifests as a shift in the correlation peak. Therefore, to make a distributed strain measurement one simply measures the shift in the cross-correlation peak for each segment along the fiber. The utilization of Rayleigh scatter from a fiber for determining strain of the fiber is known and described in US 2008/0212082 which is hereby incorporated by reference. From the determined strain of the three fibers the curvature angle θ can be determined e.g. by use of equation 1 in US 2008/0212082. It is also possible to determine the curvature of the fiber detector 110 by use of only two fibers 201. Alternatively, the fiber detector 110 may have four fibers, typically arranged as one central and three satellite fibers. This arrangement allows to correct for temperature-induced strains and to separate torsion from longitudinal strain.

Other fiber optical principles may be used for determining bending of the fiber detector 110. For example, optical fibers 201 with fiber Bragg gratings may be used. Similarly, to the Rayleigh scattering, the fiber Bragg gratings cause a change in the amplitude spectrum of reflected light which change is caused by strain (e.g. induced by bending) of the fiber. Since the spectral characteristics of fiber Bragg gratings may be well defined a storage for storing a reference amplitude spectrum may not be required.

For the case of Bragg grating fibers and fibers where the Rayleigh scattering is exploited for measuring bending, an optical characteristic of the reflected light that are affected by bending is the amplitude spectrum of reflected light, i.e. the amplitude of the reflected or scattered light at different wavelengths. The amplitude spectrum may be monitored by a spectrometer.

Optical monitoring devices 200 based on fiber Bragg gratings or Rayleigh scattering enable determination of a curvature or bending at a given location 210 along the optical fiber detector. The Rayleigh scattering based monitoring device 200 enables a high resolution of less than 0.1 mm along the length of the optical fiber detector 110. The fiber with Bragg gratings enables a similar resolution in depending on the distance between the Bragg gratings in the fiber.

Generally, the fiber detector 110 comprises at least two fibers 201 arranged coextensive and substantially parallel to each other.

The optical monitoring device 200 may comprise a processor 220 for analyzing the measured optical characteristic for determining a curvature of the optical fiber detector. For example, the processor 220 may be configured to analyze the spectral content of the Rayleigh scattered light and for determining a value of curvature at a given location 210 along the optical fiber detector 110 by cross-correlating stored reference spectral data and measured spectral data for each fiber segment 210 as described above.

The processor 220 may be a computing device which is part of the optical monitoring device 200, e.g. the optical monitoring device may contain the light source 202, the light receiver 203 and the processor 220. Alternatively, the processor may be a stand-alone computer and the optical monitoring device may be provided with an output connector for communicating measured data to the computer.

The processor 220 may further be configured for comparing the determined curvature of the fiber detector 110 with a threshold curvature. Accordingly, if it is determined that a curvature of the fiber detector is larger than the threshold curvature then an alarm may be generated by an alarm device 221. Thus, the alarm is configured to generate an alarm if a breakdown of the guidewire is predicted or if a determined curvature exceeds a maximal allowable curvature.

The alarm 221 may be configured to display the current shape of the guidewire. In the event that a breakdown of the guidewire is predicted or if a determined curvature exceeds a threshold, the alarm may be configured to highlight—on the display—which part or location 210 of the guidewire has a too low curvature or is in the risk of a breakdown. Alternatively, the alarm may simply generate a sound if a too small curvature is detected somewhere along the fiber detector 110. A notification to the user of the guidewire, e.g. in the form of an alarm, may also specify the probability of a breakdown in the case of continued use of the guidewire.

Guidewires are subject to material fatigue and, therefore, may suddenly breakdown, i.e. break, fracture or kink. By monitoring the number of times that the guidewire is bent at a given location 210 and how much the guidewire is bent at that location it is possible to predict if a breakdown of the fiber is likely to occur. A prediction of breakdown or a determination of a time when the guidewire should not be used anymore may simply be determined by counting the number of times that the guidewire has been exposed to a bending curvature smaller than a given threshold curvature, or by summing or integrating resulting bending curvatures at a given location 210 over time.

For the purpose of predicting breakdown of the guidewire the optical monitoring device 200 may include a storage 222 for storing curvatures and theirs associated locations 210 from where the measured curvature originates. The storage may be part of the processor 222 or may be a separate component. For reusable optical detectors 110 (in contrast to single-use detectors), the storage may be detachable and kept together with the detector during refurbishing for a next use. The storage may be integrated into a packaging of the detector. The storage or packaging and the optical detector 110 itself may be equipped with a unique identifier. For the breakdown prediction the processor 222 would be configured to analyze the stored curvatures, e.g. by integrating the stored bending curvatures.

The storage 222 may store data relating to the complete evolution of bending shapes during the lifetime of the guidewire. Thereby it is possible to estimate breakdown of the guidewire on basis of the entire use of the guidewire.

Whereas a storage 222 may be used for storing bending data, a solution without a storage is also possible. Thus, instead of storing curvature data, the determined curvature data may continuously be processed according to the algorithm for predicting breakdown, e.g. by continuously summing or counting curvature values from a given location 210 and which are smaller than a given threshold.

The determination of a location 210 along the guidewire may be carried out by the processor 220, e.g. from comparison of measured reflected spectrum with the stored reference Rayleigh scatter profile since the stored Rayleigh scatter profile contains characteristics which are specific for each location 210. In case the fibers 201 contains Bragg gratings distributed along the length of the fibers, both the location of the gratings and their distinguishable spectral amplitude characteristics are known and, therefore, a change in a reflected amplitude characteristic can be assigned to a specific Bragg grating and thereby a specific location 210.

The optical monitoring device may also be used with needles and catheters by embedding or attaching the optical fiber detector with the needle or catheter. Thereby, bending of needles or catheters may be monitored for predicting breakdown. Thus, it is understood that the optical monitoring device may be used together with different flexible medical instruments 100 such as guidewires, needles and catheters. Thus, the above embodiments exemplified with guidewires apply equally to needles and catheters since the optical detector 110 can be connected to such devices in the same way as for a guidewire. That is, the needles and catheters may have lumens 102 into which the optical detector can be inserted or the optical detector 110 can be connected to such devices in other ways. As an example, catheters are often braided to improve mechanical properties. A braid is a wire or fiber mesh applied to the base tube of the catheter. The optical fibers 101 or equally the optical detector 110 may be integrated into or part of this braid.

Depending of the use of the optical fiber detector it may have a length of 5 cm (e.g. for needles) to 300 cm (for long guide wires).

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. A single processor or other unit may fulfill the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An optical monitoring device for monitoring curvature along a flexible medical instrument, the device comprises: an optical fiber detector comprising one or more optical fibers, a light source configured to inject light into the optical fibers, a light receiver configured to measure an optical characteristic of reflected light from the optical fibers, where the optical fibers are configured so that the optical characteristic of the reflected light is affected by bending of the fibers, a processor configured to analyze the measured optical characteristic to determine a curvature of the optical fiber detector at a plurality of locations, wherein each of the plurality of locations is a different location from others of the plurality of locations, compare the curvature with a threshold curvature for each of the plurality of locations and produce an indication when the curvature is smaller than the threshold curvature, determine each associated location of the plurality of locations along the optical fiber detector for each of the curvatures, store previous curvatures, indications and the associated locations along the fiber detector in a storage, produce a separate count or sum of the stored curvatures and the indications for each of the associated locations over time to predict breakdown of the flexible medical instrument, and produce an indication when the counted or summed curvatures from any given associated location of the associated locations over time predict breakdown of the flexible medical instrument.

2. The optical monitoring device according to claim 1, where the device further comprises an alarm configured to generate an alarm signal when a breakdown is predicted or when the curvature exceeds a maximal allowable curvature.

3. A flexible medical instrument comprising the optical monitoring device according to claim 1, where the optical fiber detector extends along the flexible medical instrument and within an outer surface of the flexible medical instrument.

4. A method for monitoring curvature along a flexible medical instrument, the method comprising acts of: arranging an optical fiber detector comprising one or more optical fibers along the flexible medical instrument, injecting light into the one or more optical fibers using a light source, measuring an optical characteristic of reflected light from the optical fibers using a light receiver, where the optical fibers are configured so that the optical characteristic of the reflected light is affected by bending of the fibers, analyzing the measured optical characteristic for determining a curvature of the optical fiber detector at a plurality of locations, wherein each of the plurality of locations is a different location from others of the plurality of locations, comparing the curvature with a threshold curvature for each of the plurality of locations and producing an indication when the curvature is smaller than the threshold curvature, determining each associated location of the plurality of locations along the optical fiber detector for each of the curvatures, storing previous curvatures, indications and the associated locations along the fiber detector in a storage, producing a separate count or sum of the stored curvatures and the indications for each of the associated locations over time to predict breakdown of the flexible medical instrument, and producing an indication in response to the counted or summed curvatures from any given associated location of the associated locations over time indicating a predicted breakdown of the flexible medical instrument.

* * * * *